US012564574B2

(12) United States Patent
Park et al.

(10) Patent No.: US 12,564,574 B2
(45) Date of Patent: Mar. 3, 2026

(54) PHARMACEUTICAL COMPOSITION FOR PREVENTING OR TREATING PARKINSON'S DISEASE, COMPRISING 2-(4-(1-HYDROXYPROPANE-2-YL)PHENYL) ISOINDOLINE-1-ONE COMPOUND

(71) Applicant: YEP BIO CO. LTD., Anyang-si (KR)

(72) Inventors: Chi Hu Park, Hwaseong-si (KR); Myungjoo Yu, Seoul (KR); Hyoung Shik Kim, Hwaseong-si (KR)

(73) Assignee: YEP BIO CO. LTD., Anyang-si (KR)

( * ) Notice: Subject to any disclaimer, the term of this patent is extended or adjusted under 35 U.S.C. 154(b) by 528 days.

(21) Appl. No.: 17/928,943

(22) PCT Filed: Mar. 25, 2021

(86) PCT No.: PCT/KR2021/003722
§ 371 (c)(1),
(2) Date: Dec. 1, 2022

(87) PCT Pub. No.: WO2021/246627
PCT Pub. Date: Dec. 9, 2021

(65) Prior Publication Data
US 2023/0226022 A1     Jul. 20, 2023

(30) Foreign Application Priority Data

Jun. 3, 2020    (KR) ........................ 10-2020-0066977

(51) Int. Cl.
| | |
|---|---|
| *A61K 31/4035* | (2006.01) |
| *A23L 33/00* | (2016.01) |
| *A23L 33/10* | (2016.01) |
| *A61K 49/22* | (2006.01) |
| *A61P 25/16* | (2006.01) |

(52) U.S. Cl.
CPC .......... *A61K 31/4035* (2013.01); *A23L 33/10* (2016.08); *A23L 33/40* (2016.08); *A61K 49/22* (2013.01); *A61P 25/16* (2018.01)

(58) Field of Classification Search
None
See application file for complete search history.

(56) References Cited

U.S. PATENT DOCUMENTS

| | | |
|---|---|---|
| 2004/0044063 A1 | 3/2004 | Stockwell et al. |
| 2009/0312323 A1 | 12/2009 | Heemskerk et al. |
| 2011/0301150 A1 | 12/2011 | Park et al. |
| 2017/0095451 A1 | 4/2017 | Cho et al. |
| 2019/0030053 A1 | 1/2019 | Kang |

FOREIGN PATENT DOCUMENTS

| | | |
|---|---|---|
| CN | 106146484 A | 11/2016 |
| JP | 2009-530306 A | 8/2009 |
| KR | 10-2010-0097059 A | 9/2010 |
| KR | 10-2014-0000733 A | 1/2014 |
| KR | 10-2019-0016938 A | 2/2019 |
| WO | 2007-109211 A1 | 9/2007 |

OTHER PUBLICATIONS

Ascherio. Lancet Neurology, 2016, 15, 1257-1272 (Year: 2016).*
Balke. Molecular Neurobiology, 2020, 57, 685-697, published Aug. 24, 2019 (Year: 2019).*
Su, X. et al., "PGC-la promoter methylation in Parkinson's disease", PloS one. 2015, vol. 10, No. 8, document No. e0134087, pp. 1-24.

* cited by examiner

*Primary Examiner* — Noble E Jarrell
(74) *Attorney, Agent, or Firm* — Revolution IP, PLLC

(57) ABSTRACT

The present invention relates to a pharmaceutical composition for preventing or treating Parkinson's disease, comprising a 2-(4-(1-hydroxypropane-2-yl)phenyl) isoindoline-1-one compound or a pharmaceutically acceptable salt thereof, wherein the pharmaceutical composition for preventing or treating Parkinson's disease can increase the protein level of PGC-la in the brain of an individual by successfully passing through the blood-brain barrier (BBB).

6 Claims, 9 Drawing Sheets

[FIG. 1]

[FIG. 2]
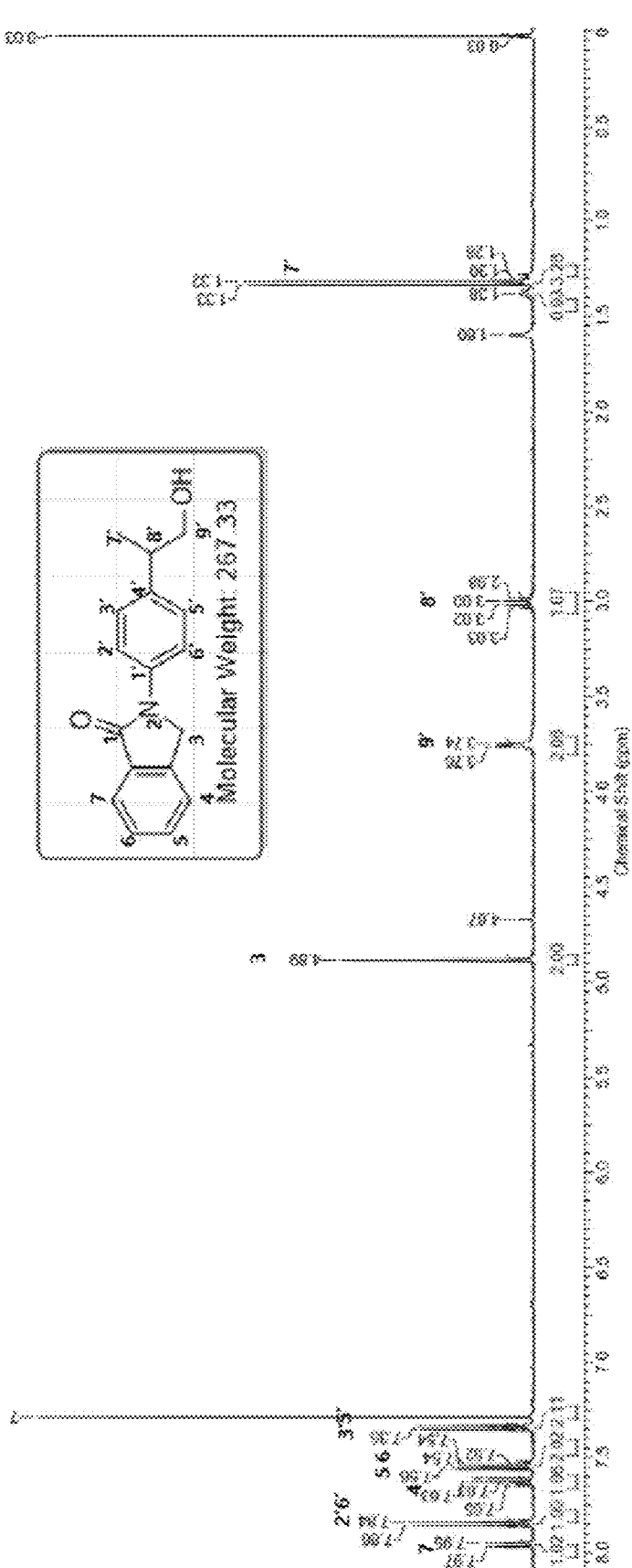

[FIG. 3]

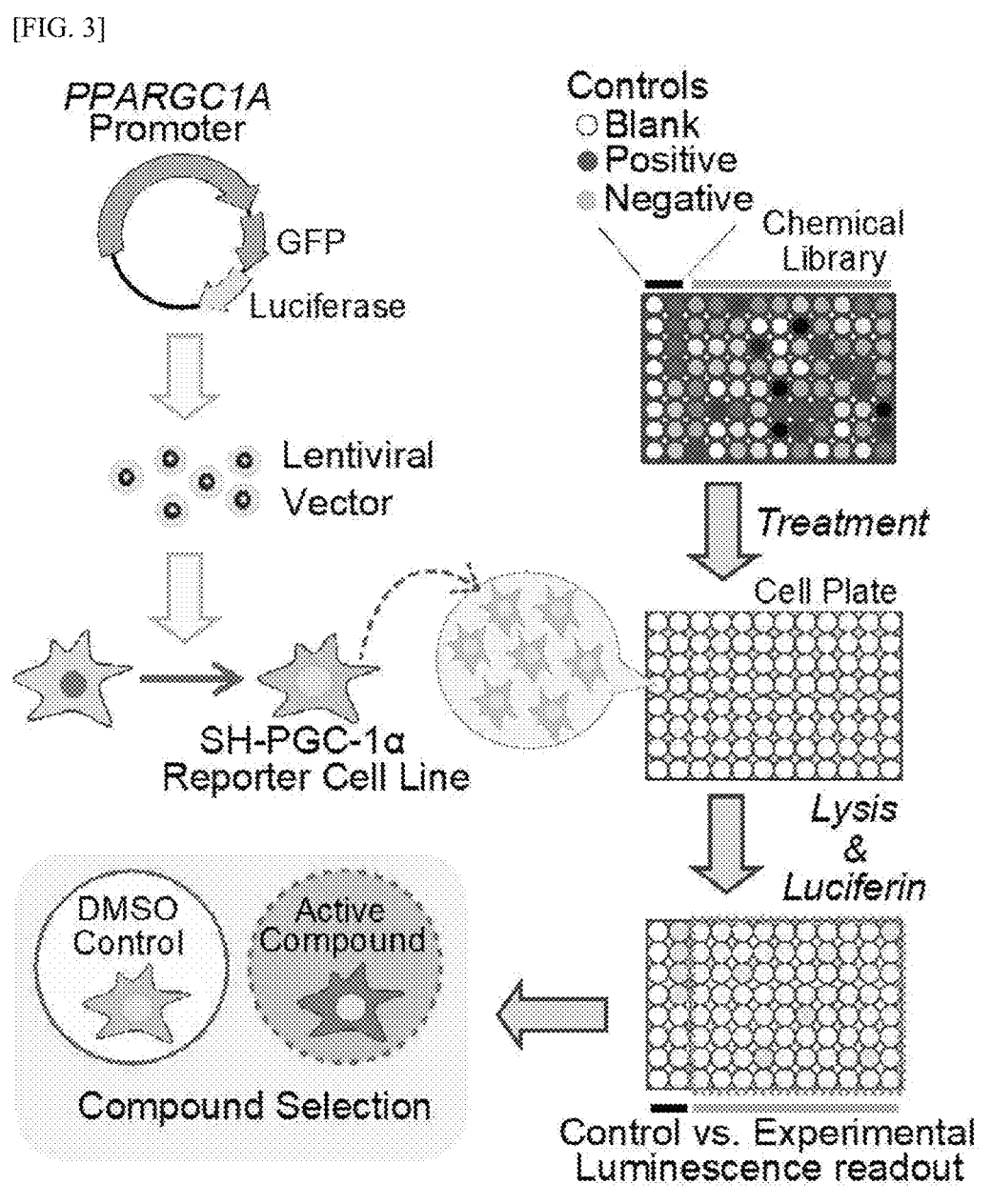

PPARGC1A Promoter
GFP
Luciferase

Lentiviral Vector

SH-PGC-1α Reporter Cell Line

DMSO Control    Active Compound

Compound Selection

Controls
○ Blank
● Positive
◐ Negative
Chemical Library

Treatment

Cell Plate

Lysis & Luciferin

Control vs. Experimental Luminescence readout

[FIG. 5]
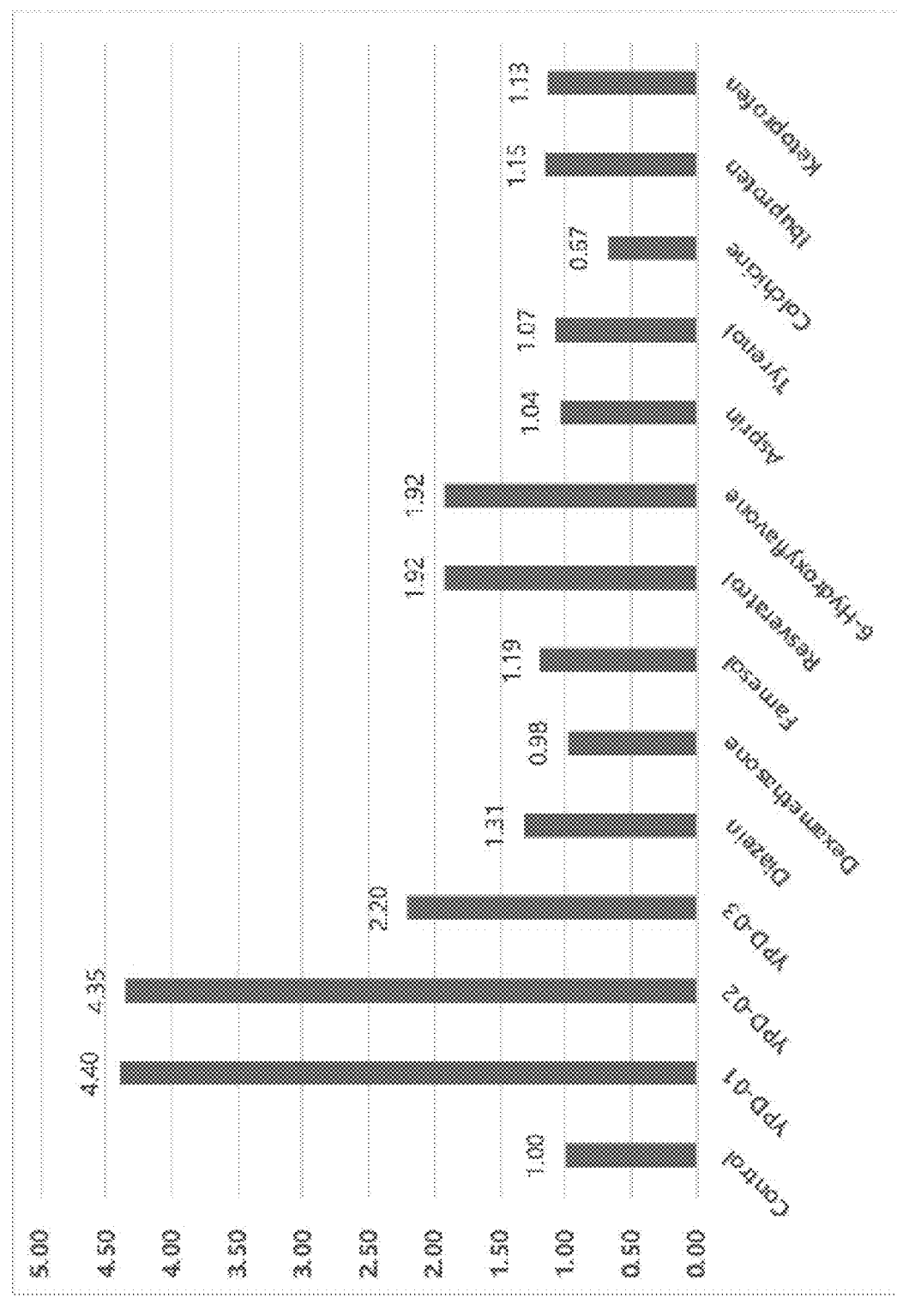

[FIG. 6]
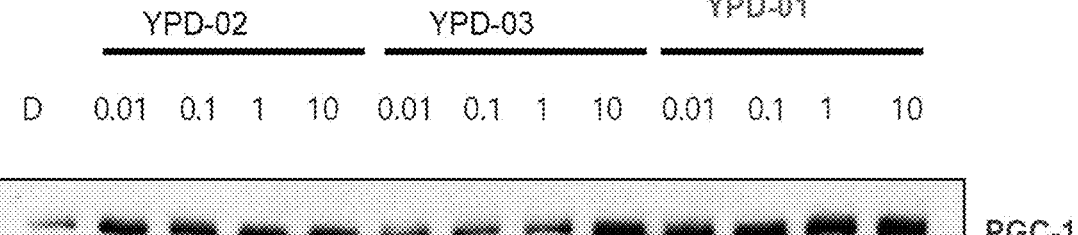
[FIG. 7]
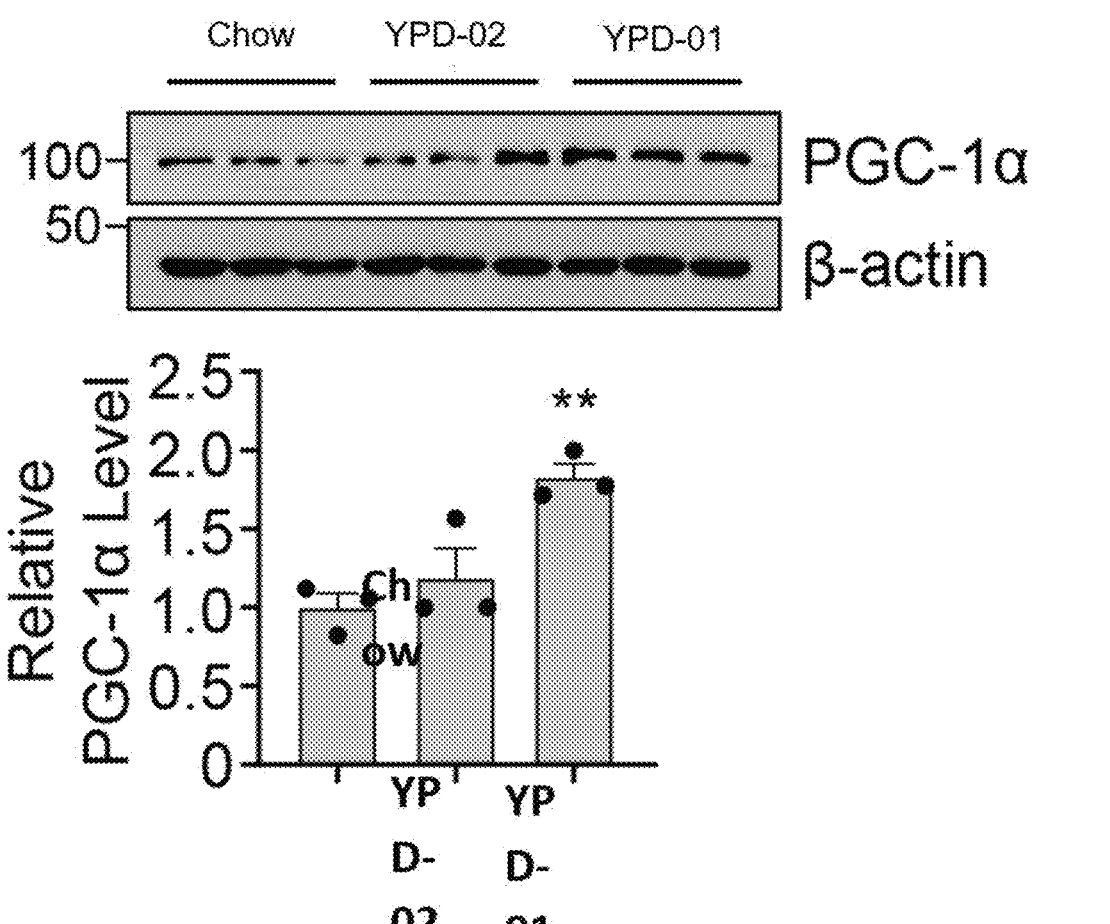

FIG. 8
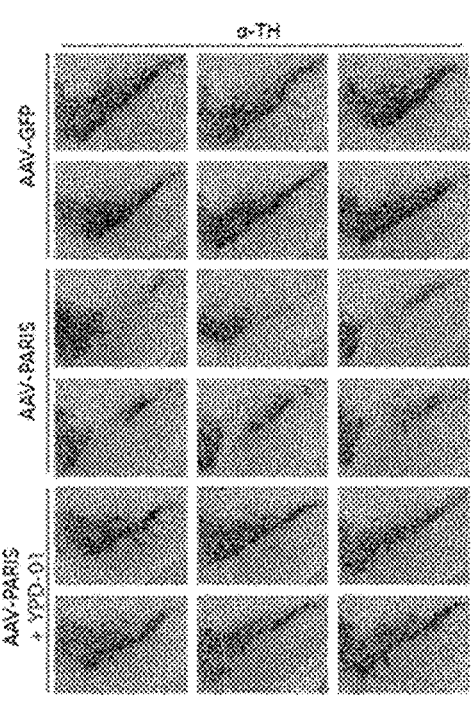
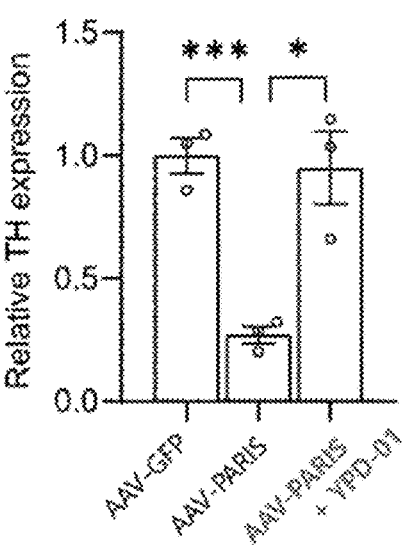
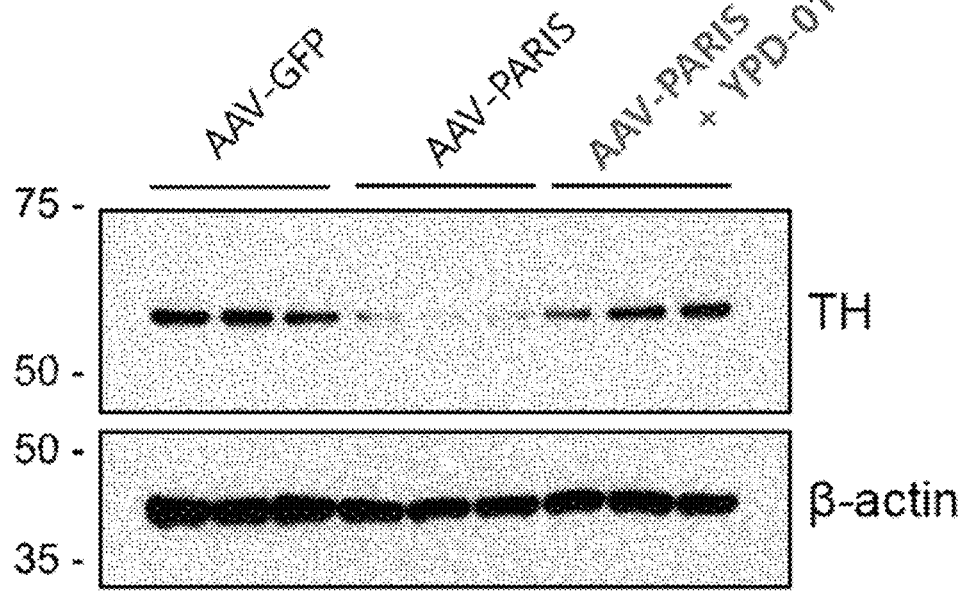

PHARMACEUTICAL COMPOSITION FOR PREVENTING OR TREATING PARKINSON'S DISEASE, COMPRISING 2-(4-(1-HYDROXYPROPANE-2-YL)PHENYL) ISOINDOLINE-1-ONE COMPOUND

CROSS REFERENCE TO PRIOR APPLICATIONS

This application is the 35 U.S.C. 371 national stage of international application PCT/KR2021/003722 filed on Mar. 25, 2021 which claims priority to Korean Patent Application No. 10-2020-0066977 filed on Jun. 3, 2020. The entire contents of each of the above-identified applications are hereby incorporated by reference.

TECHNICAL FIELD

The present disclosure relates to a pharmaceutical composition for preventing or treating Parkinson's disease, including a 2-(4-(1-hydroxypropan-2-yl)phenyl) isoindolin-1-one compound or a pharmaceutically acceptable salt thereof.

BACKGROUND ART

Parkinson's disease, a disease whose main symptoms are tremors (shaking), rigidity, ataxia (slowed movements), and prolonged unstable posture, is a chronic disease caused by a lack of neurotransmitters called dopamine in the brain and one of the degenerative diseases in the central nervous system, which is started with modification in the substantia nigra pars *compacta* in the midbrain and accompanied by its pathophysiological symptoms such as reduction in brain volume and aggregation of α-synuclein (αSyn) as well as imperfect gait, hand tremor, and rigid behavior.

Most treatment strategies for Parkinson's disease were limited to managing the symptoms of motor functions with drugs such as L-DOPA or dopamine receptor agonists as well as deep brain stimulation. In addition, these therapies at the current research level have failed to prevent the gradual death of dopaminergic neurons (DAs).

Recently, on the other hand, when it comes to death and survival of cells, research related to the function of peroxisome proliferator-activated receptor-γ coactivator-1α (PGC-1α) and various diseases that may be caused by dysregulation of PGC-1α has been reported.

Neurodegenerative diseases such as Alzheimer's disease, Parkinson's disease, Huntington's disease, and Lou Gehrig's disease are caused by the gradual loss of function and death of neurons, and the overall symptoms of these diseases are due to the loss of certain parts of neurons. Unlike the hyperactivity due to neurodegeneration observed in PGC-1α knock-out mice and the damaged areas that are less observed in the cerebral cortex, it is noticed that PGC-1α is directly related to neurodegenerative diseases based on the damaged sites that are markedly found in corpus striatum in the brain.

Also, in addition to these findings, the identification of vacuolar lesions in the central nervous system in PGC-1α knock-out mice shows that PGC-1α plays a crucial role in maintaining neuronal functions.

Reduced expression of PGC-1α increases the expression of BACE1, which produces beta-amyloid by degrading and cleaving the progenitor protein of amyloid that causes Alzheimer's disease and increases the amount of beta-amyloid, thereby leading to mitochondrial hypofunction and cell death. Single-nucleotide mutations in the PGC-1α gene are highly correlated with an increase in the risk factors that develop Parkinson's disease and Huntington's disease and are known to decrease expression of PGC-1α genes in patients with Alzheimer's disease, Parkinson's disease, and Huntington's disease.

Recently, there has been a rising interest in treatment methods for Parkinson's disease by pharmacologically activating PGC-1α for its functional mechanisms, which are closely related to those neurodegenerative diseases.

PRIOR ART DOCUMENT

Patent Document (Patent Document 1) Korean Patent No. 10-1384642

DISCLOSURE OF THE INVENTION

Technical Goals

An object of the present disclosure is to provide a composition capable of preventing or treating Parkinson's disease in a subject, as an expression of PGC-1α is enhanced in the brain by including a 2-(4-(1-hydroxypropan-2-yl) phenyl) isoindoline-1-one compound.

Technical Solutions

The present disclosure provides a pharmaceutical composition for preventing or treating Parkinson's disease, including a compound represented by the following Chemical Formula 1 or a pharmaceutically acceptable salt thereof as an active ingredient.

[Chemical Formula 1]

In addition, the composition may increase the expression of peroxisome proliferator-activated receptor-γ coactivator-1α (PGC-1α).

In addition, the composition may have a formulation selected from the group consisting of a solution, suspension, syrup, emulsion, liposome, acid, powder, granule, tablet, sustained-release agent, and capsule.

In addition, the composition may be a composition for oral administration and have a formulation of a drug carrier or sustained-release agent, including liposomes.

In addition, the composition may be a composition for parenteral administration and have a formulation of a drug carrier or sustained-release agent including liposomes and ultrasonic contrast agents.

In addition, the compound represented by Chemical Formula 1 is 2-(4-(1-hydroxypropan-2-yl)phenyl) isoindoline-1-one.

According to another aspect of the present disclosure, healthy functional food for alleviating Parkinson's disease, including a compound represented by the Chemical Formula 1 as an active ingredient, is provided.

According to another aspect of the present disclosure, a method of preventing or treating Parkinson's disease, including administering a composition including a compound represented by the Chemical Formula 1 or a pharmaceutically acceptable salt thereof, to an individual may be provided.

Advantageous Effects

The pharmaceutical composition for preventing or treating Parkinson's disease, according to the present disclosure, successfully passes through the blood-brain barrier (BBB) and increases expression of PGC-1α, which has a neuroprotective ability in the brain of an individual, thereby exhibiting the effect of preventing or treating Parkinson's disease of a subject.

BRIEF DESCRIPTION OF DRAWINGS

FIG. 1 shows a reaction scheme illustrating the synthetic process of a 2-(4-(1-hydroxypropan-2-yl)phenyl) isoindolin-1-one compound according to the present disclosure.

FIG. 2 shows NMR data for identifying a structure after synthesizing a 2-(4-(1-hydroxypropan-2-yl)phenyl) isoindolin-1-one compound according to the present disclosure.

FIG. 3 shows a schematized compound screening experimental method in Example 2.

FIG. 5 shows a graph illustrating the result of experiments performed with 14 drugs that increase the activity of the PGC-1α promoter by 2.5 times or more.

FIG. 6 shows an image of proteins from an immunoblot after treating an SH-SY5Y cell line with compounds (Example 4).

FIG. 7 shows an immunoblot of PGC-1α protein in the substantia nigra (SN) of mice fed with compounds (Example 4).

FIG. 8 shows immunohistochemistry and immunoblot in the brain tissue of Parkinson's disease model mice fed with a compound-included diet (Example 5).

BEST MODE FOR CARRYING OUT THE INVENTION

Figure 4:
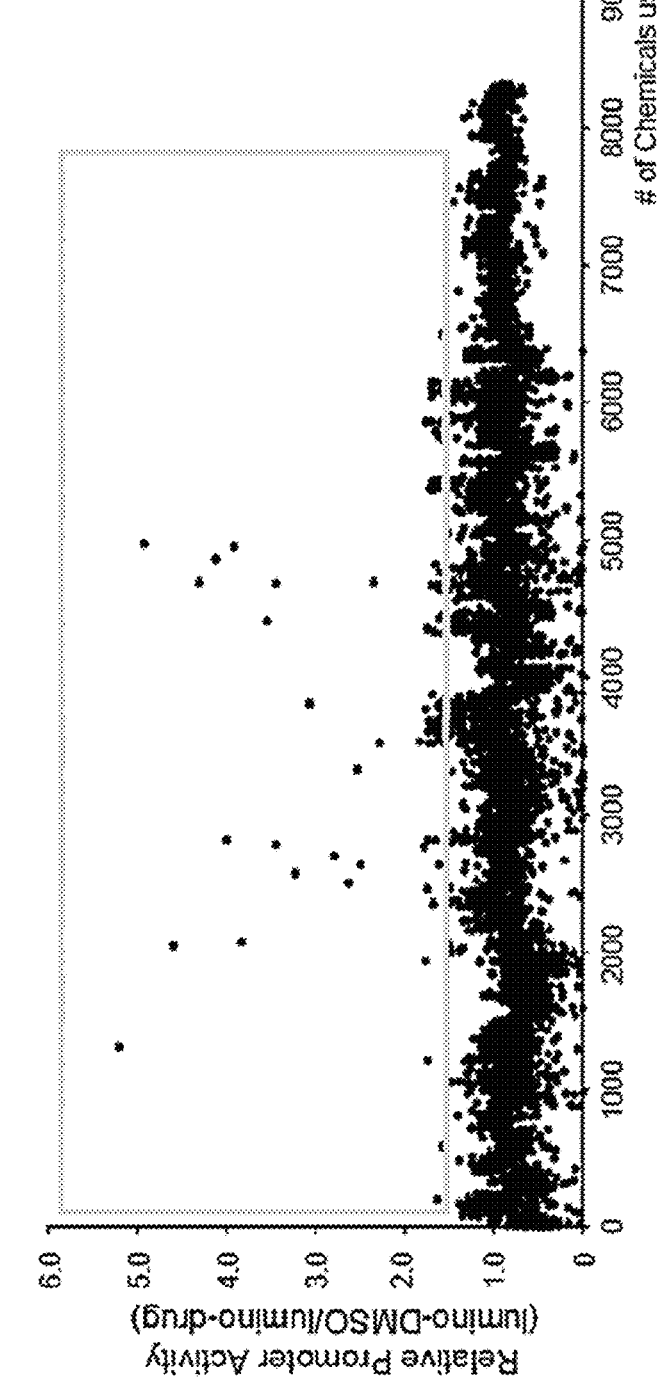
FIG. 4 shows an activity measurement result graph for the PGC-1α promoter via luciferase assay in Example 2.

Since the present disclosure may be subjected to various modifications and have various example embodiments, specific example embodiments will be illustrated in the drawings and described in detail. However, this is not intended to limit the present disclosure to specific example embodiments and should be understood to include all modifications, equivalents, and substitutes included in the spirit and scope of the present disclosure. In describing the present disclosure, when it is determined that the detailed description of the related known techniques may obscure the gist of the present disclosure, the detailed description thereof will be omitted.

The present disclosure provides a pharmaceutical composition for preventing or treating Parkinson's disease, including a compound represented by the following Chemical Formula 1 or a pharmaceutically acceptable salt thereof as an active ingredient.

[Chemical Formula 1]

Hereinafter, the pharmaceutical composition for preventing or treating Parkinson's disease according to a specific embodiment of the present disclosure will be described in more detail.

Conventional treatment strategies for Parkinson's disease have been limited to managing symptoms of motor functions using drugs such as L-DOPA or dopamine receptor agonists and deep brain stimulation, which have failed to prevent the gradual death of dopaminergic neurons (DAs).

Accordingly, the present inventors completed the present disclosure by identifying that when a specific derivative compound is administered, the compound successfully passes through the BBB to increase the activity of the PGC-1α promoter as well as the level of protein expression of PGC-1α in the brain.

The present disclosure provides a pharmaceutical composition for preventing or treating Parkinson's disease, including the 2-(4-(1-hydroxypropan-2-yl)phenyl) isoindoline-1-one compound or a pharmaceutically acceptable salt thereof as an active ingredient.

PGC-1α is a key regulator of mitochondrial function to co-regulate transcriptional programs that are important for mitochondrial biogenesis and protect mitochondria from oxidative stress. Such PGC-1α level decreases in patients with Parkinson's disease, and the decline in the PGC-1α level in Parkinson's disease is considered to be due to methylation on the PGC-1α promoter.

On the other hand, PGC-1α knock-out mice are more sensitive to the degenerative effect of 1-methyl-4-phenyl-1, 2,3,6-tetrahydropyridine (MPTP), a Parkinson's disease neurotoxin, overexpression of PGC-1α is known to have a protective effect against N-methyl-4-phenylpyridinium ion (MPP+) toxin, an active metabolite of MPTP, and overexpression of PGC-1α is also known to exhibit a protective effect against α-synuclein, MPTP, oxidative stress and rotenone-induced degeneration.

The PGC-1α reactive gene is downregulated in dopaminergic neurons derived from patients with Parkinson's disease, which is thought to suggest that the PGC-1α plays an important role in the cause of Parkinson's disease; and, when PARIS, a substrate of Parkin which is a causative protein of Parkinson's disease, is overexpressed, the loss of dopamine neurons is suppressed by PGC-1α overexpression, which is thought to show that PGC-1α is the main target of Parkin in dopaminergic neurodegeneration.

Therefore, defects in PGC-1α signaling have emerged as an important cause of dopaminergic degeneration in Parkinson's disease, and reduction of PGC-1α due to dysfunction of Parkin may be a prime target for the prevention or treatment of Parkinson's disease.

In Example 2 of the present disclosure, activity measurement results of the promoter of PGC-1α through a luciferase assay were shown (FIG. 4), and the results of experiments performed with 14 drugs that increase the activity of PGC-1α promoter by 2.5 times or more were shown, wherein the activity of 2-(4-(1-hydroxypropan-2-yl)phenyl) isoindoline-1-one which is a compound represented by Chemical Formula 1 was the highest (FIG. 5).

In addition, in Example 4 of the present disclosure, according to the image analysis of immunoblot performed after treating an SH-SY5Y cell line with various concentrations of compounds (0, 0.01, 0.1, 1.0, 10 μM, 48 hours), it was found that 2-(4-(1-hydroxypropan-2-yl)phenyl) isoindoline-1-one increases the amount of PGC-1α protein even in the low concentrations (FIG. 6).

In addition, as shown in immunoblot for PGC-1α protein in the SN of mice fed with Chow, Indoprofen, or YPD-01 (2-(4-(1-hydroxypropan-2-yl)phenyl) isoindoline-1-one) diet (0.5% w/w), it was found that 2-(4-(1-hydroxypropan-2-yl)phenyl) isoindoline-1-one successfully passed through the BBB and statistically significantly increased the protein expression of PGC-1α in the SN of mice (Example 4, FIG. 7).

In addition, in Example 5 of the present disclosure, after feeding Parkinson's disease model mice with Chow or YPD-01 diet (0.5% w/w) and then sectioning the brain using a microtome after collecting the brain, AAV-PARIS injection remarkably killed dopamine neurons that was significantly inhibited by the administration of YPD-01 diet (FIG. 8).

Figure 9:
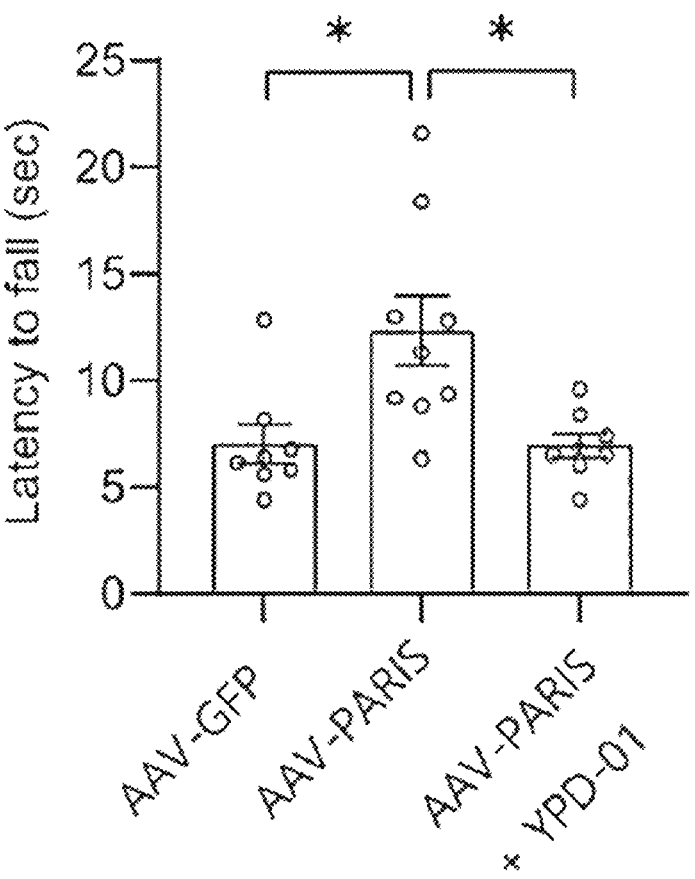
FIG. 9 shows a pole test of Parkinson's disease model mice fed with a compound-included diet (Example 6).

In addition, in Example 6 of the present disclosure, as a result of performing a pole test after feeding Parkinson's disease model mice with Chow or YPD-01 diet (0.5% w/w), the time required for AAV-PARIS8-injected mice to come down from the top of the pole took twice longer than AAV-GFP-injected mice, and it was found that behavioral abnormality disappeared due to YPD-01 administration (FIG. 9).

Figure 10:
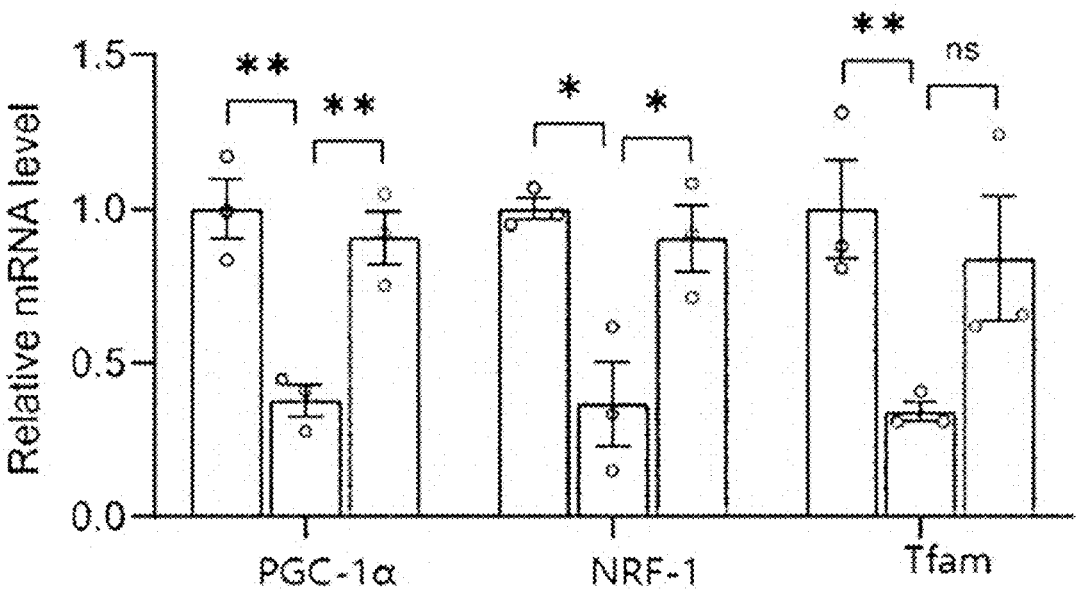
FIG. 10 shows the expression of PGC-1α and the primary target genes of PGC-1α in Parkinson's disease model mice fed with a compound-included diet (Example 7).

In addition, in Example 7 of the present disclosure, as a result of measuring the expression of PGC-1α and the target genes of PGC-1α after feeding Parkinson's disease model mice with Chow or YPD-01 diet (0.5% w/w), over-expression of PARIS by AAV-PARIS brought about suppression of PGC-1α expression and reduced expression of target genes thereof. It was found that the suppression of expression of PGC-1α and main target genes of PGC-1α (NRF-1, Tfam) by PARIS in the substantia nigra of mice fed with YPD-01 diet was significantly restored (FIG. 10).

On the other hand, the compound represented by the following Chemical Formula 1 is 2-(4-(1-hydroxypropan-2-yl)phenyl) isoindoline-1-one

[Chemical Formula 1]

Figure 1:
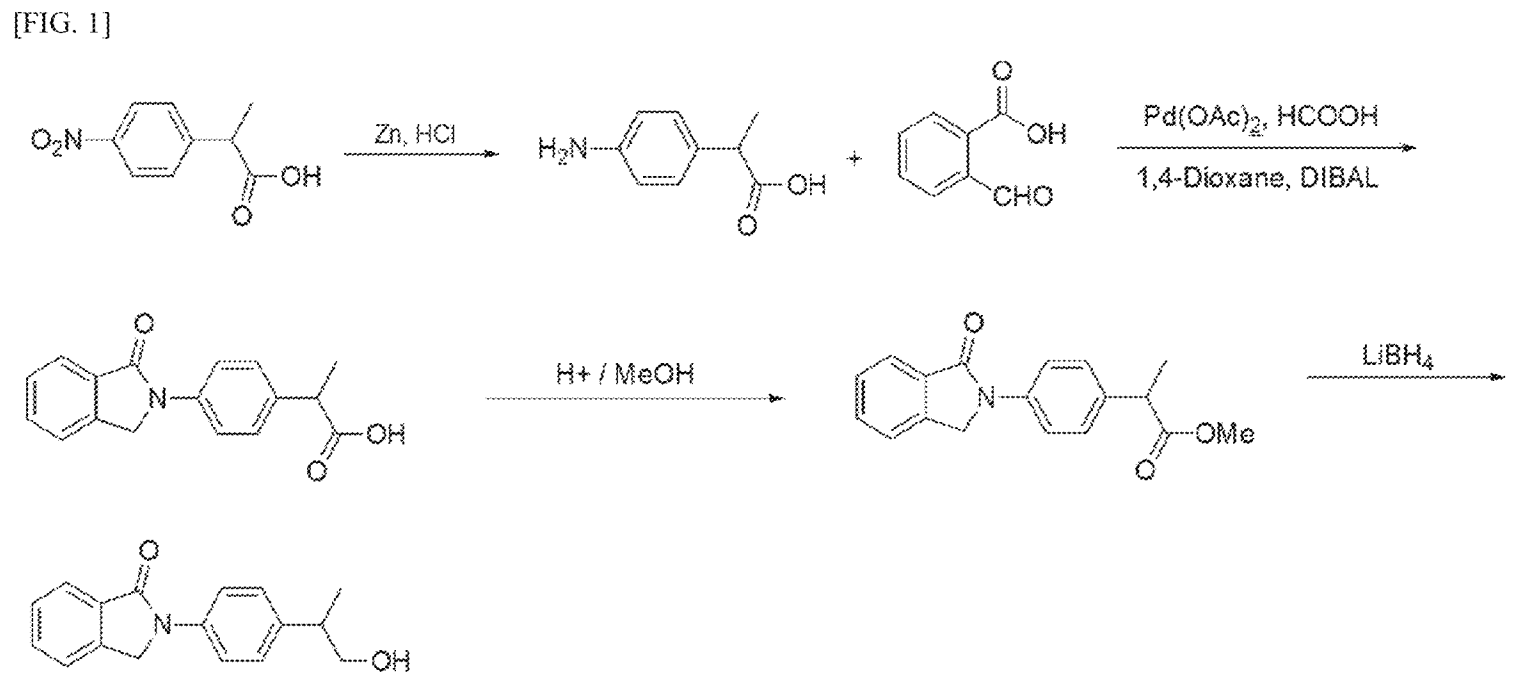

FIG. 1 is a synthesis reaction scheme of the 2-(4-(1-hydroxypropan-2-yl)phenyl) isoindoline-1-one compound, and FIG. 2 is NMR data of identifying a structure after synthesizing the compound.

In the pharmaceutical composition of the present disclosure, the active ingredient is a compound of Chemical Formula I, a pharmaceutically acceptable salt thereof, a hydrate, or a solvate.

The term "pharmaceutically acceptable salt" as used herein refers to a salt of the compound that induces the desired pharmacological effect, that is, the expression of PGC-1α. Such salts may be formed by using inorganic acids such as hydrochloride, hydrobromide, and hydroiodide, as well as organic acid such as acetate, adipate, alginate, aspartate, benzoate, benzene sulfate, p-toluene sulfonate, bisulfate, sulfamate, sulfate, naphthylate, butyrate, citrate, camporate, camposulfonate, cyclopentane propionate, digluconate, dodecyl sulfate, ethane sulfonate, fumarate, glucoheptanoate, glycerophosphate, hemisulfate, heptanoate, hexanoate, 2-hydroxyethane sulfate, lactate, maliate, methane sulfonate, 2-naphthalene sulfonate, nicotinate, oxalate, tosylate, and undecanoate. The term "pharmaceutically acceptable hydrate" as used herein refers to a hydrate of the compound having the desired pharmacological effect, and the term "pharmaceutically acceptable solvate" as used herein refers to a solvate of the compound having the desired pharmacological effect. The hydrate and solvate may also be prepared using the acid described above.

On the other hand, suitable carriers, excipients, and diluents that are commonly used to prepare the pharmaceutical composition may further be included. In addition, it may be formulated according to conventional methods into oral formulations such as acids, granules, tablets, capsules, suspensions, emulsions, syrups, and aerosols, as well as forms of external agents, suppositories, and sterile injection solutions.

Carriers, excipients, and diluents that may be included in the composition are lactose, dextrose, sucrose, sorbitol, mannitol, xylitol, erythritol, maltitol, starch, gum acacia, alginate, gelatin, calcium phosphate, calcium silicate, cellulose, methylcellulose, microcrystalline cellulose, polyvinylpyrrolidone, water, methyl hydroxybenzoate, propyl hydroxybenzoate, talc, magnesium stearate, and mineral oil. When the composition is formulated, it may be prepared using diluents or excipients such as fillers, extenders, binders, wetting agents, disintegrants, surfactants, and the like that are commonly used.

The pharmaceutical composition, according to the present disclosure, may be administered in a pharmaceutically effective amount. The term "pharmaceutically effective amount" as used herein refers to an amount sufficient to treat a disease at a reasonable benefit/risk ratio applicable to medical treatment. The type of disease of a patient, severity, activity of the drug, sensitivity to the drug, administration time, route of administration, excretion rate, treatment period, factors including concomitant drugs, and other factors well-known in the medical field may determine the effective dose level.

The pharmaceutical composition, according to the present disclosure, may preferably be administered simultaneously, separately, or sequentially with the concomitant drug in order to enhance the therapeutic effect and may be administered by single or multiple doses. Considering all the factors above, it is important to administer in an amount that may derive the maximum effect with the minimum amount without side effects, which may be easily determined by those skilled in the art. Specifically, the effective amount of the pharmaceutical composition according to the present disclosure may vary depending on the age, sex, condition, and weight of a patient, absorption of an active ingredient in vivo, inactivity rate and excretion rate, disease type, and concomitant drugs.

The pharmaceutical composition of the present disclosure may be administered to an individual by various routes. All modes of administration are predictable, including, for example, oral administration, intranasal administration, transbronchial administration, arterial injection, intravenous injection, subcutaneous injection, intramuscular injection, or intraperitoneal injection.

The pharmaceutical composition of the present disclosure is determined according to the type of drug that is the active ingredient, along with various related factors such as the disease to be treated, the route of administration, the age, sex, weight, and severity of the disease of a patient.

In another aspect of the present disclosure, the present disclosure provides a method of inhibiting neuroinflammation, including administering the pharmaceutical composition to an individual. The term "individual" as used herein refers to a subject in need of treatment for a disease, and more specifically, a human or non-human primate and mammals such as a mouse, dog, cat, horse, and cow.

In addition, the pharmaceutical composition according to an example embodiment of the present disclosure may be a formulation selected from the group consisting of a solution, suspension, syrup, emulsion, liposome, acid, powder, granule, tablet, sustained-release agent, and capsule.

Moreover, the composition may be a composition for oral administration and have a formulation of a drug carrier or sustained-release agent including liposomes. In addition, the composition may be a composition for parenteral administration and have a formulation of a drug carrier or sustained-release agent including liposomes and ultrasound contrast agents.

The pharmaceutical composition of the present disclosure may be encapsulated in liposomes to provide stability in the formulation for drug delivery. The liposomes used herein may be prepared by mixtures of polyols, surfactants, phospholipids, fatty acids, and water.

Polyols used in liposomes are not particularly limited and preferably include propylene glycol, dipropylene glycol, 1,3-butylene glycol, glycerin, methylpropanediol, isoprene glycol, pentylene glycol, erythritol, xylitol, and sorbitol, but most preferably propylene glycol.

Any surfactant known in the art may be used to prepare liposomes, such as anionic surfactants, cationic surfactants, amphoteric surfactants, and nonionic surfactants may be used, preferably anionic surfactants and nonionic surfactants are used. Specific examples of anionic surfactants include alkyl acyl glutamate, alkyl phosphate, alkyl acetylate, dialkyl phosphate, and trialkyl phosphate. Specific examples of nonionic surfactants include alkoxylated alkyl ethers, alkoxylated alkyl esters, alkyl poly glycosides, poly glyceryl esters, and sugar esters.

Phospholipids, another component used in the preparation of liposomes, are used as amphiphilic lipids, including natural phospholipids and synthetic phospholipids, preferably lecithin. Fatty acids used in liposome preparation are high-grade fatty acids, preferably saturated or unsaturated fatty acids of the C12-22 alkyl chain, including, for example, lauric acid, myristic acid, palmitic acid, stearic acid, oleic acid, and linoleic acid. The water used in the preparation of liposomes is generally deionized distilled water.

Preparation of liposomes may be performed by various methods known in the art, but most preferably, the preparation is performed by applying a mixture including the components to a high-pressure homogenizer. The liposome system prepared thereby has the advantage of dissolving various types of poorly soluble substances and stabilizing unstable substances, thereby maximizing drug delivery.

The pharmaceutical composition of the present disclosure may be prepared as a sustained-release agent to increase medication adherence by reducing the number of doses of the drug through continuous maintenance of the effective blood concentration of the active ingredient.

Sustained-release agents are prepared by including sustained-release carriers and other adjuvants in addition to the active ingredients of the present disclosure. Various sustained-release carriers known in the art may be used for the sustained-release carriers that may be used herein, but it is preferably polyethylene oxides.

In addition to other adjuvants, dilution carriers commonly used in the pharmaceutical field may be included. Examples of dilution carriers used for such purpose include lactose, dextrin, starch, microcrystalline cellulose, calcium mono hydrogen phosphate, calcium carbonate, sugars and silicon dioxide, and other glidants such as zinc stearate or magnesium to increase fluidity or other adjuvants available in the pharmaceutical field may be included.

The composition of the present disclosure may be for an administration to a subject in which expression of peroxisome proliferator-activated receptor-γ coactivator-1α (PGC-1α) is reduced.

According to another aspect of the present disclosure, a health functional food for ameliorating Parkinson's disease, including the compound represented by Chemical Formula 1 as an active ingredient, may be provided.

When the composition of the present disclosure is prepared as a food composition or functional food composition, it may include not only the compound of Chemical Formula I as an active ingredient but also components commonly added during food preparation, including, for example, proteins, carbohydrates, fats, nutrients, seasonings, and flavoring agents. Examples of carbohydrates described above include monosaccharides, such as glucose and fructose; disaccharides, such as maltose, sucrose, and oligosaccharides; and polysaccharides, such as conventional sugars like dextrin and cyclodextrin, as well as sugar alcohols such as xylitol, sorbitol, and erythritol. As flavoring agents, natural flavoring agents and synthetic flavoring agents (saccharin, aspartame, etc.) may be used. In addition, when the food composition of the present disclosure is prepared as a drink, citric acid, liquid fructose, sugar, glucose, acetic acid, malic acid, fruit juice, Eucommia bark extract, jujube extract, licorice extract, and the like may be further included in addition to the compound of Chemical Formula I of the present disclosure.

According to another aspect of the present disclosure, a method of preventing or treating Parkinson's disease, including administering, to a subject, a preparation including a compound represented by the Chemical Formula 1 is provided.

MODES FOR CARRYING OUT THE INVENTION

Hereinafter, a preferred example embodiment of the present disclosure will be described in detail with reference to the accompanying drawings. However, these example embodiments are intended only to illustrate the present disclosure, and the scope of the present disclosure will not be construed as being limited by these example embodiments.

Example 1: Preparation of a Reporter Cell Line and a Human Cell Line

In order to prepare lentiviruses for preparation of stable reporter SH-SY5Y cells (SH-PGC-1α-Luc), 1-kb pGL3-PGC-1α promoter-luciferase was cloned to pGreenFire (System Biosciences), and a lentivirus construct was first prepared (provided by Akyosi Fukamizu from University of Tsukuba, Japan).

HEK293T cells cultured in 15 cm dish were subjected to transfection with 32 μg of pGreenFire vector, 9 μg of VSVg envelope, 6.25 μg of Prev, and 12.5 μg of pMDL.

After 48 hours, viral supernatants were collected and concentrated using ultracentrifugation, and viral pellets were dissolved with PBS. SH-SY5Y cells were treated with concentrated virus and screened with puromycin (1 μg/ml) a day later.

To culture human neuroblasts SH-SY5Y cells (ATCC, Manassas, VA), 10% FBS (vol/vol, Welgene Gold Serum, cat #S 001-07) and DMEM (Welgene fresh media DMEM, cat #LM 001-05) including antibiotics were used, wherein the culture was performed in an incubator (Forma Direct Heat CO2 incubator, Thermo Scientific) at 37° C. in the presence of 5% carbon dioxide.

Example 2: Compound Screening and Data Analysis to Identify Compounds that Increase the Expression of PGC-1α

The library of 8,320 compounds was sorted (Korean Chemical Bank, Daegeon) out of 230,000 drugs in consideration of the properties of the drug, which is a combined library of 6,000 drugs and 2,320 spectrum collections (Microsource) whose quality is controllable by liquid chromatography mass spectroscopy (LC-MS) (60% clinically approved drugs, 25% natural products, 15% bioactive drugs).

To determine the suitability of the experiment for high-throughput screening (HTS), standard parameters including signal-to-background (S/B) ratio, daily rate of change, and rate of change for each plate, as well as Z' factor and coefficient of variation (CV) were measured.

All HTS experiments followed the NIH guidelines (High-Throughput Screening Assay Guidance Criteria).

SH-PGC-1α-Luc was dispensed in a white, flat-bottomed 96-well plate, where culture was performed to accommodate 10,000 cells in 100 μl of DMEM (10% FBS+penicillin/ streptomycin (P/S)) per well, and the cells were stabilized in an incubator at 37° C. in the presence of 5% $CO_2$ for 12 hours.

The next day, each drug was added to 50 μl of warmed DMEM to the final concentration of 20 μM, then 50 μl of DMEM was removed from the cell-containing plate, and 50 μl of drug-containing DMEM was added (final concentration of 10 μM). Cells were then exposed to the drug for 48 hours, and luciferase activity was measured using SteadyGlo reagent (Promega).

Each plate had three internal controls, Daidzein (positive control, 10 μM), and two negative controls (treated and untreated with DMSO). The luciferase measurement values for each well are shown in the ratio based on the average value of the untreated controls.

The Z' factor of this experiment showed a value between 0.5 and 1. The difference between each well, plate, and experiment day was measured by comparing the change in the control. DMSO resistance, stability of a reagent, and experimental conditions were also checked to prove effectiveness.

The activity measurement results for the PGC-1α promoter via luciferase assay are shown in FIG. 4. Luciferase activity was measured by reading the first data, wherein the comparison was made based on DMSO, and the blue square box in FIG. 4 indicates drugs that are more than 1.5 times activated.

The results of the experiment performed with 14 drugs that increase the activity of PGC-1α promoter by 2.5 times or more are shown in FIG. 5 (YPD-01 in FIG. 5 is 2-(4-(1-hydroxypropan-2-yl)phenyl) isoindoline-1-one which is a compound represented by the Chemical Formula 1 herein, YPD-02 is 2-[4-(3-oxo-1H-isoindol-2-yl)phenyl]propanoic acid, and YPD-03 is isopropyl 2-(4-(1-oxoisoindolin-2-yl) phenyl) propanoate).

Example 3: SH-SY5Y Cell and Tissue Sampling for Immunoblot

RIPA buffer was added to the SH-SY5Y cells and SN of C57L/6N mice, followed by homogenization with a homogenizer. Thereafter, the freezing and melting process was repeated three times, and quantification was performed using a BCA kit based on BSA to check the total amount of protein.

Lysates were identified by adding 2× SDS sample buffer, heating at 95° C. for 10 minutes to perform immunoblot, and then treating the desired protein with antibody.

In the immunoblot experiment, the darkness of the band was measured using the ImageJ (NIH, Bethesda, MO, USA, http://rsb.info.nih.gov/ij/) program, and statistical analysis was performed using the darkness of the protein band in proportion to the loading control. The statistical analysis was performed using the GraphPad Prism version 7 (GraphPad Software) program. For the data, the unpaired two-tailed student's t-test was applied, wherein p<of 0.05 indicates statistical significance.

In Example 4 below, when the sample shows a statistical significance by the student's t-test compared to the control, it was marked with an asterisk (*p<0.05,  p<0.01, and * p<0.001).

Example 4: Effect of 2-(4-(1-hydroxypropan-2-yl) phenyl)isoindoline-1-one in an SH-SY5Y Cell Line and the Mouse Brain As shown in Example 3, an image of an immunoblot performed after treating the SH-SY5Y cell line with compounds (10 μM, 48 hours) is shown in FIG. 6.

As shown in FIG. 6, it was found that YPD-02 (2-[4-(3-oxo-1H-isoindol-2-yl)phenyl]propanoic acid) and YPD-03 (isopropyl 2-(4-(1-oxoisoindolin-2-yl)phenyl) propanoate) increased the amount of PGC-1α protein in accordance with an increase in the drug concentration (0.01, 0.1, 1, 10 μM), while YPD-01 (2-(4-(1-hydroxypropan-2-yl)phenyl) isoindolin-1-one) increased the amount of PGC-1α protein regardless of the concentration.

In FIG. 7, an immunoblot is shown for protein derived from the SN of mice fed with Chow, YPD-02 (2-[4-(3-oxo-1H-isoindol-2-yl)phenyl]propanoic acid), or YPD-01 (2-(4-(1-hydroxypropan-2-yl)phenyl) isoindoline-1-one) diet (0.5% w/w) for 1 week (quantitative graph quantified with β-actin/data was expressed as mean±SEM/statistical significance was measured by applying the unpaired two-tailed student t-test. * p<0.05, ** p<0.01.).

From the results in FIG. 7, it was found that YPD-01 (2-(4-(1-hydroxypropan-2-yl)phenyl) isoindoline-1-one) successfully passed through BBB and increased the protein level of PGC-1α in the SN of mice.

Example 5: Inhibitory Effect of YPD-01 on the Death of Dopamine Neurons in Parkinson's Disease Model Mice To prepare Parkinson's disease model mice, AAV-PARIS was stereotaxically injected into the substantia nigra area. The mice were fed with Chow or YPD-01 (2-(4-(1-hydroxy-propan-2-yl)phenyl) isoindoline-1-one) diet (0.5% w/w) for 4 weeks, and then the brain was collected and sectioned using a microtome. Dopaminergic neurons were visualized by carrying out a reaction in the mouse brain tissue sliced into 35 μm sections using TH antibody, a neuronal dopamine marker, then exposed to Vectastine ABC (Vector biolabs) and DAB (Sigma) solutions. Six rats were used in each experiment.

-Introduction of Adeno-Associated Virus (AAV) Via Stereotaxic Injection

100 μl of pentobarbital (10 mg/ml) was injected into the abdomen of 8-week-old mice for anesthetization, mouse pericranium was peeled off, and then the left brain (X: 1.2, Y: -3.2, Z: -4.5) and right brain (X: 1.2, Y: 3.2, Z: -4.5) regions were marked based on the bregma. The marked portion was drilled, and the virus was injected slowly (30 seconds per 0.2 μl) through a syringe. After injecting the virus into the left brain, followed by a 2-minute standby, the same procedure was performed on the other side. After the surgical suture, the mice were carefully monitored, and breeding was followed in the cage until the recovery.

-Immunoblot (Western Blot, WB)

Midbrains of mice into which AAV-PARIS was stereotaxically injected and which were fed with Chow or YPD-01 diet (0.5% w/w) for 4 weeks were collected, and protein was extracted with RIPA lysis buffer. The concentration of protein was adjusted to 4 mg/ml by the BCA verification method. Electrophoresis was performed in 7% polyacrylamide gel by mixing with 2× Laemmli sample buffer. After transfer, the primary antibody and HRP-conjugated secondary antibody were attached, followed by development using an ECL solution. AAV-GFP was used as a control of AAV-PARIS.

-Immunohistochemistry

Mouse brain tissues sliced into 35 um ice sections were subjected to a reaction with tyrosine hydroxylase (TH) antibody, a neuronal dopamine marker, at 4° C. overnight, and a reaction was carried out the next day using biotin-conjugated secondary antibodies, followed by the development of the shape of dopamine neurons by exposing to Vectastain ABC (Vector Biolabs) and DAB (Sigma) solution. The developed brain tissue was placed on a glass slide and examined under a microscope.

As shown in FIG. 8, AAV-PAIS injection significantly killed dopamine neurons, and in mice fed with YPD-01 diet, the death of dopamine neurons was meaningfully inhibited. Consistent with the result shown in immunohistochemistry, as a result of performing immunoblot in the substantia nigra of mice using TH antibody, a dopamine neuronal marker (quantitative graph quantified with β-actin/data was expressed as mean±SEM/statistical significance was measured by applying one-way ANOVA. * p<0.05, *** p<0.001), it was re-identified that the death of dopamine neurons by AAV-PARIS was inhibited by YPD-01 as confirmed by the result found in immunohistochemistry.

Example 6: Inhibitory Effect on Behavioral Abnormality in Parkinson's Disease by YPD01

In order to identify whether YPD-01 is effective in inhibiting the death of dopamine neurons and Parkinson's disease-like behavioral abnormality in the Parkinson's disease model, as shown in Example 5 above, a pole test, which is the most reliable behavioral experiment, was performed.

-Pole Test

To investigate behavioral abnormality, Parkinson's disease model mice were transferred to a pole test cage to have the mice adapted for 3 minutes, and then the mouse tails were held and placed on the tip of a vertically erected pole. The time from the moment the mouse took off its hind foot from the tip of the pole until the mouse came down to the floor was measured.

As shown in FIG. 9, due to due to potential AAV-PARIS-induced death of dopamine neurons, the time taken for mice injected with AAVPARIS to come down from the top of the pole was about twice longer than that of mice injected with AAV-GFP (used as a control). The symptoms of behavioral abnormality disappeared by YPD-01 intake, consistent with inhibition of death of the dopamine neurons described in Example 5 above (data was expressed as mean±SEM/statistical significance was measured by applying one-way ANOVA. *p<0.05).

Example 7: Verification that YPD-01 Increases Expression of PGC-1α in Parkinson's Disease Model Mice In the animal model experiment set up as in Example 5, whether the expression of PGC-1α and the main target genes (NRF-1, Tfam) of PGC-1α increases due to YPD-01 intake was measured by RT-qPCR method.

-Reverse Transcription Quantitative Real-Time Polymerase Chain Reaction (RT-qPCR)

The midbrain of mice into which AAV-PARIS was stereotaxically injected and which were fed with Chow or YPD-01 diet for 4 weeks was collected, and RNA was extracted using the total RNA extraction kit (Intron Biotechnology). cDNA was synthesized using the cDNA synthesis kit (Enzynomics) and oligo dT from the extracted RNA. Using primers and SYBR green (Qiagen) reagents for the gene to be analyzed, gene expression in Rotor gene Q (Qiagen) was quantified via qPCR.

As identified in FIG. 10, PARIS overexpression by AAV-PARIS caused suppression of PGC-1α expression and reduced expression of its target genes. PARIS-induced suppression of expression of PGC-1α and main target genes (NRF-1, Tfam) of PGC-1α was significantly recovered in the substantia nigra of mice fed with YPD-01 (quantitative graph quantified with β-actin/data was expressed as mean±SEM/statistical significance was measured by applying one-way ANOVA. * p<0.05, ** p<0.01; ns, not significant).

As a specific part of the present disclosure is described in detail above, it will be apparent to those skilled in the art that such specific techniques are only preferred embodiments and the scope of the present disclosure is not limited thereby. Thus, the substantial scope of the present disclosure will be defined by the appended claims and their equivalents.

The invention claimed is:

1. A method of treating Parkinson's disease in a subject in need thereof, comprising:

administering a pharmaceutical composition comprising a compound represented by the following Chemical Formula 1,

[Chemical Formula 1]

or a pharmaceutically acceptable salt thereof as an active ingredient to the subject,

wherein the pharmaceutical composition is to be administered to the subject in which expression of peroxisome proliferator-activated receptor-γ coactivator-1α (PGC-1α) is reduced.

2. The method of claim 1, wherein the pharmaceutical composition increases the expression of peroxisome proliferator-activated receptor-γ coactivator-1α (PGC-1α).

3. The method of claim 1, wherein the pharmaceutical composition has a formulation selected from the group consisting of a solution, suspension, syrup, emulsion, liposome, acid, powder, granule, tablet, sustained-release agent, and capsule.

4. The method of claim 3, wherein the pharmaceutical composition is a composition for oral administration and has a formulation of a drug carrier or sustained-release agent comprising liposomes.

5. The method of claim 3, wherein the pharmaceutical composition is a composition for parenteral administration and has a formulation of a drug carrier or sustained-release agent comprising liposomes and ultrasonic contrast agents.

6. A method of ameliorating Parkinson's disease to a subject in need thereof, comprising:
administering a healthy functional food comprising a compound represented by the following Chemical Formula 1,

[Chemical Formula 1]

as an active ingredient to the subject.

\* \* \* \* \*